United States Patent [19]

Steinhaus et al.

[11] Patent Number: 5,255,186
[45] Date of Patent: Oct. 19, 1993

[54] SIGNAL AVERAGING OF CARDIAC ELECTRICAL SIGNALS USING TEMPORAL DATA COMPRESSION AND SCANNING CORRELATION

[75] Inventors: Bruce M. Steinhaus, Parker; Randy T. Wells, Littleton, both of Colo.

[73] Assignee: Telectronics Pacing Systems, Inc., Englewood, Colo.

[21] Appl. No.: 740,922

[22] Filed: Aug. 6, 1991

[51] Int. Cl.$^5$ .............................................. G06F 15/42
[52] U.S. Cl. .................................. 364/413.06; 128/700
[58] Field of Search .................. 364/413.06, 413.05; 128/696, 700, 702, 703, 704, 705, 708

[56] References Cited

U.S. PATENT DOCUMENTS 4,202,340  5/1980  Langer et al. .................. 128/419 D

OTHER PUBLICATIONS

D. Lin et al., "Identification of Ventricular Tachycardia Using Intracavitary Ventricular Electrograms: Analysis of Time and Frequency Domain Patterns", *PACE*, vol. 11, pp. 1592-1606 (1988).

B. M. Steinhaus et al., "Detection of Ventricular Tachycardia Using Scanning Correlation Analysis", *PACE*, vol. 13, pp. 1930-1936 (Dec. 1990, Part II).

*Primary Examiner*—Donald E. McElheny, Jr.
*Attorney, Agent, or Firm*—Gottlieb, Rackman & Reisman

[57] ABSTRACT

A method and apparatus for aligning periodic cardiac signal waveforms for the purpose of signal averaging over a number of cardiac cycles. The aligning method and apparatus sense cardiac electrical signals over a number of cardiac cycles, store a template characterizing these signals, reduce the data rate of the same sensed signals by temporal data compression, and store a compressed template sequence. Subsequently, the method and apparatus perform signal averaging by monitoring cardiac electrical signals, storing samples of these signals, temporally compressing these samples and scan correlating the compressed samples with the previously stored compressed template sequence to derive correlation coefficients. Thereafter, the method and apparatus utilize the maximum correlation coefficient to roughly align the monitored waveform with the averaged signal, and then they scan correlate a portion of the noncompressed monitored waveform adjacent to the maximum correlation coefficient with a corresponding portion of the non-compressed template to provide precise alignment of the monitored waveform with the averaged signal.

26 Claims, 6 Drawing Sheets

FIG. 5B.
TEMPLATE — NSR (1000Hz)
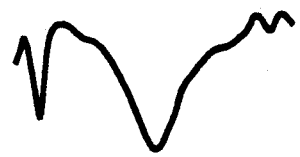
FIG. 5A.
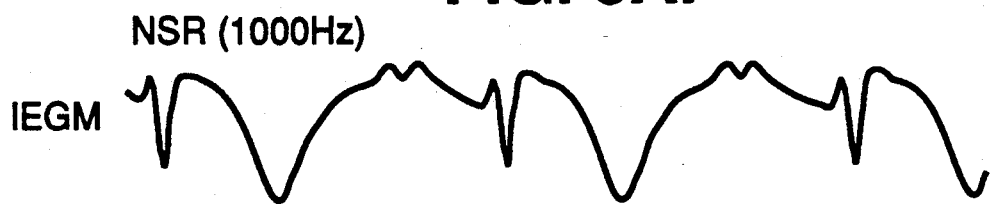
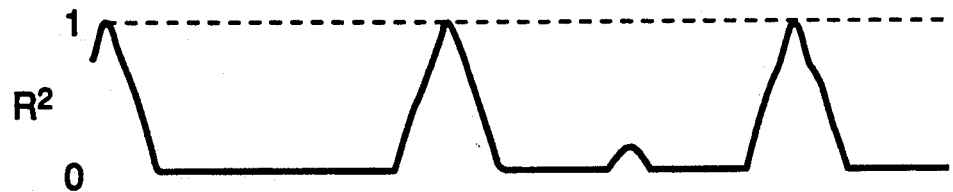
FIG. 5C.

FIG. 5E.
TEMPLATE — NSR (50Hz)
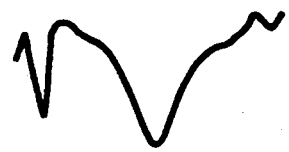
FIG. 5D.
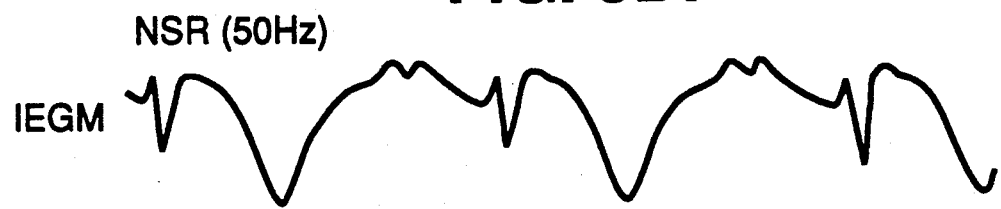
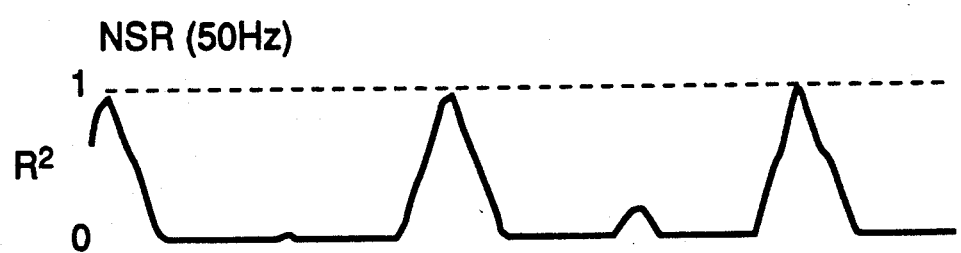
FIG. 5F.

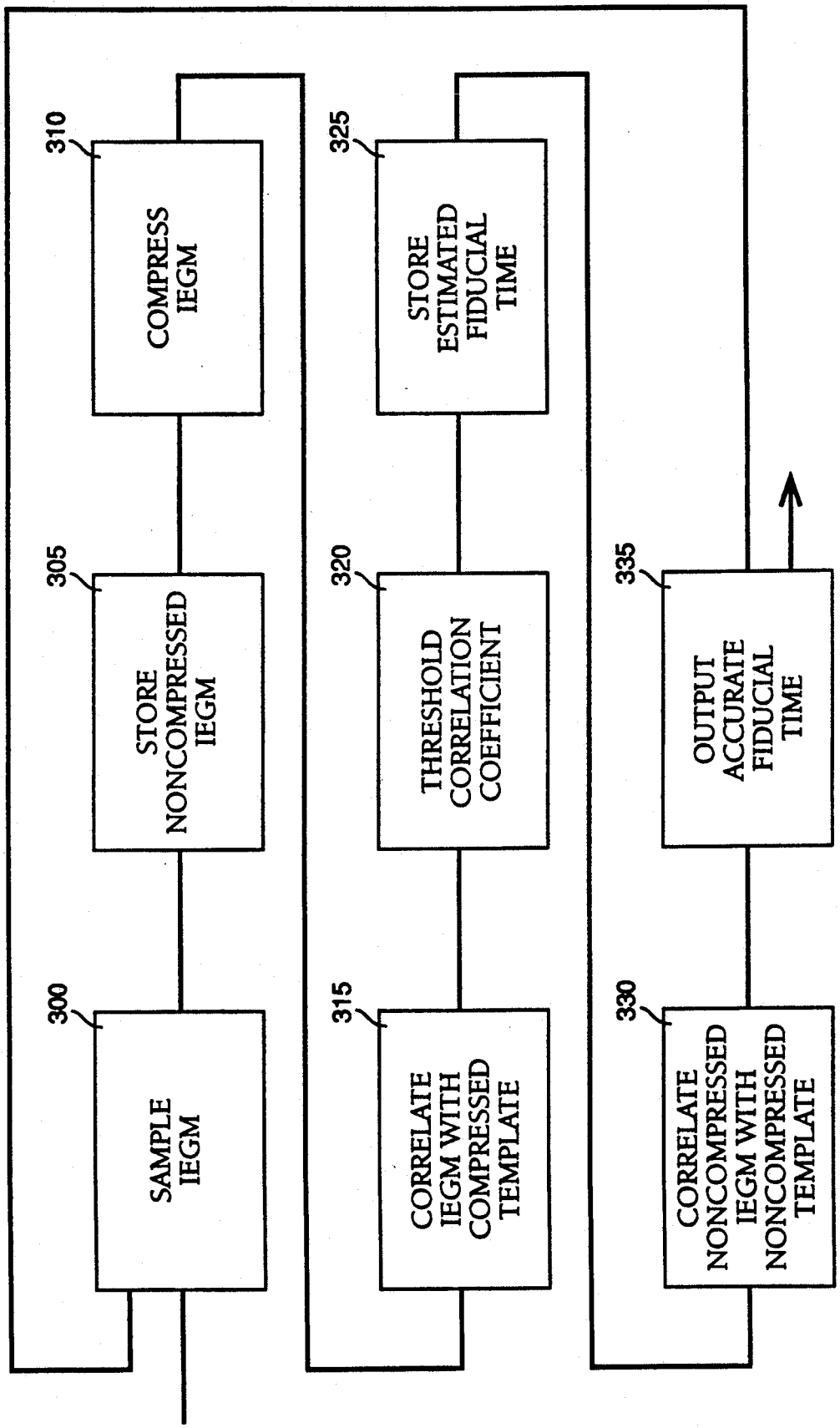

SIGNAL AVERAGING OF CARDIAC ELECTRICAL SIGNALS USING TEMPORAL DATA COMPRESSION AND SCANNING CORRELATION

TECHNICAL FIELD

This invention relates generally to cardiac control and monitoring devices which utilize signal averaging to analyze cardiac signals, and more particularly to systems within such devices which align signals sampled during one cardiac cycle with signals acquired in other cardiac cycles in a manner which reduces the number of individual computation operations required and thereby reduces energy needs.

BACKGROUND OF THE INVENTION

A cardiac medical device may monitor cardiac electrical signals for many purposes. A cardiac control instrument analyzes cardiac signals to determine how well the cardiovascular system is performing. As a result of this analysis, the instrument responds to some predetermined signal characteristics by automatically initiating control operations. A cardiac signal measurement device analyzes cardiac signals to illuminate diagnostic information within a sensed cardiac waveform. The time sequence of cardiac signal amplitudes which are sensed by a device constitutes the morphology, or shape, of the cardiac waveform. Some components of the cardiac signal with significant diagnostic utility have small amplitudes in relation to other signal elements. Often, important diagnostic information within the cardiac waveform is obscured by noise.

Signal averaging is a technique for detecting low amplitude periodic signals which are obscured by random signals having a much larger amplitude. This technique involves the averaging of multiple occurrences of the periodic waveform. Signal averaging reduces the amplitude of an additive random noise signal by a factor proportional to the inverse of the square root of the number of the signal-averaged heart beats. Signal averaging reduces the influence of beat to beat changes, respiratory variations and other changes not synchronized to the electrocardiogram and allows detection of low amplitude periodic signals otherwise hidden in noise.

These benefits of signal averaging are available only if the analyzing device can temporally align, with extreme accuracy, the cardiac signal components within each cardiac cycle which are periodic and have a period of a single cardiac cycle. The timing marker for each cardiac cycle which defines proper alignment is called a fiducial time. Timing offsets between waveforms from different cardiac cycles will cause the averaged signal to lessen rather than increase the desired signal morphology amplitude.

One method of aligning the waveforms from different cardiac cycles is to correlate the sensed and sampled waveform from the current cardiac cycle with the stored signal average, in a manner described in greater detail below. The resulting correlation coefficients for the samples provide alignment information in two ways; first, they are utilized to determine whether the current signal is sufficiently similar to the averaged signal to perform averaging in this cycle; and, second, they are used to determine the position within the averaged signal at which to add each current sample. The correlation coefficients for the samples are mutually compared with the coefficients of the other samples to determine the maximum correlation coefficient. If the maximum correlation coefficient is too small, the current waveform is too dissimilar to be averaged into the averaged signal. Otherwise, the current waveform is averaged into the averaged signal according to the location of the maximum correlation coefficient for the cycle.

Correlation involves the summation of the products of point-by-point multiplications of two waveform sequences for the purpose of deriving a standard of similarity between the two waveform sequences. Unfortunately, correlation analysis requires such computational complexity that it is impractical in an implanted device. Because the device expends energy on each computational step and correlation requires so many computations, the lifetime of an implanted device performing correlation would be unreasonably short or the battery size too large for practical usage.

One modified technique for performing standard correlation is by multiplying the waveform sequences in a section-by-section manner called piecewise correlation analysis, which provides for a reduction in the number of required computations by limiting the correlation procedure to operate only in the vicinity of the R-wave. In one example of piecewise correlation, a signal processing system defines a representative "normal" signal by measuring a ventricular electrogram signal template when the heart is functioning with a normal sinus rhythm. The system specifies this template by "windowing" the waveform, detecting the QRS complex of the cardiac signal and storing a predetermined number of samples before and after the QRS complex. For example, a waveform window may include 64 samples, which contain the QRS complex and are acquired at a 1000 Hz rate. The system averages a number of these waveform windows for a preset number of cardiac cycles with the QRS complex for each cardiac cycle occurring at the same sample location within the window. After sampling and storing the template waveform, the system samples the ventricular electrogram at the same rate and for the same number of samples as was done when acquiring the template samples. The system correlates these samples with the average sinus rhythm template on a beat-by-beat basis.

The piecewise correlation technique requires that the QRS complexes of the template and the sample electrogram are aligned. In piecewise correlation analysis, accurate template alignment is very important. In practice, alignment errors greater than four to five milliseconds cause a large and unpredictable variability in correlation coefficients. Furthermore, alignment errors frequently are not recognized since a sensing determination aligned on some feature other than the R-wave may still result in a high correlation output.

Reliable template alignment is not a simple procedure. For example, a system which aligns R-waves according to a measured point of maximum intracardiac electrogram (IEGM) amplitude or corresponding to the peak derivative of the signal does not provide adequate alignment due to the large variability in amplitude and slope of the signal waveform. Signal processing of the cardiac signal to clarify the position of the R-wave using a variety of search windows and filtering techniques is helpful for particular signal morphologies but no single alignment procedure is adequate for all patients. The wide variability in cardiac signal morphologies for different patients and also for different times for the same patient cause these alignment difficulties.

Furthermore, a system which performs window alignment based on the peak cardiac signal amplitude is susceptible to errors from T-wave sensing. Occasional patients may display T-waves which are consistently larger in amplitude than R-waves. Consequently, windows may align on the T-wave or may align on the R- and T-waves in alternating cardiac cycles. Systems which align the template and sample signals based on the location of the sensed peak derivative commonly err from five to ten milliseconds because of the noisy nature of derivative signals. When combined with low pass filtering, alignment by peak derivative sensing improves somewhat but remains unacceptable.

The small size of the piecewise correlation window which is necessary to provide the computational efficiency for an implantable device leads to an additional source of alignment error. As the device performs piecewise correlation over a single cardiac cycle it may detect multiple peaks, possibly caused by T-wave sensing or detection of multiple peaks associated with the R-wave.

Full scanning correlation, in which a continuously sampled cardiac signal is correlated with a template sequence having a predetermined length smaller than the duration of the shortest possible cardiac cycle, avoids the alignment problems inherent in piecewise correlation. Unfortunately, full scanning correlation requires an excessive number of computations, and therefore too much power drain, for an implantable device.

It is, therefore, a primary object of the present invention to provide a system for accurately determining fiducial times for aligning cardiac electrical waveforms in signal averaging applications.

It is a further object of the present invention to provide for processing of cardiac electrical signal data in a compressed form, thereby reducing the computational and energy requirements of the apparatus.

Further objects and advantages of this invention will become apparent as the following description proceeds.

SUMMARY OF THE INVENTION

Briefly stated, and in accordance with one aspect of the present invention, a method and apparatus are provided for aligning cardiac electrical signal waveforms from a patient's heart to facilitate signal averaging of cardiac signals. The aligning method and apparatus of this invention sense cardiac electrical signals over a number of cardiac cycles, store a template characterizing these signals, reduce the data rate of the same sensed signals by performing temporal data compression, and store a compressed template. Subsequently, the method and apparatus perform signal averaging by monitoring cardiac electrical signals, storing samples of these signals, temporally compressing these samples and scan correlating the compressed samples with the previously stored compressed template sequence to derive correlation coefficients. Thereafter, the method and apparatus utilize the maximum correlation coefficient to roughly align the monitored waveform with the averaged signal, and then they scan correlate a portion of the noncompressed monitored waveform adjacent to the maximum correlation coefficient with a corresponding portion of the noncompressed template to provide precise alignment of the monitored waveform with the averaged signal.

In accordance with another aspect of the invention, during performance of temporal data compression in the foregoing method and apparatus, the number of data time samples to be presented for scan correlation is reduced by subtracting each of a predetermined number of consecutive noncompressed samples of input cardiac electrical signal from the most recently determined compressed sample, where the predetermined number represents the compression ratio. The method and apparatus then store each of the noncompressed samples and its associated absolute difference value from each subtracting step result and mutually compare each of the stored absolute difference values to determine the largest absolute difference. The current compressed sample then is set to the value of the stored noncompressed sample associated with the largest absolute difference.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIGS. 5A, 5B, 5C, 5D, 5E, and 5F are sample illustrations of signal waveforms acted upon or produced at different stages of processing by the compressed correlation processor of the present invention, in which FIG. 5A is a 1000-Hz normal sinus rhythm cardiac signal, FIG. 5B is a 1000 Hz normal sinus rhythm template, FIG. 5C, is a 1000 Hz correlation result, FIG. 5D is a compressed 50 Hz normal sinus rhythm cardiac signal, FIG. 5E is a compressed 50 Hz normal sinus rhythm template, and FIG. 5F is a compressed 50 Hz correlation coefficient; and, FIG. 6 is a flow diagram illustrating a preferred procedure for performing cardiac waveform alignment for signal averaging using the scanning correlation technique of the present invention.

DETAILED DESCRIPTION

Figure 1:
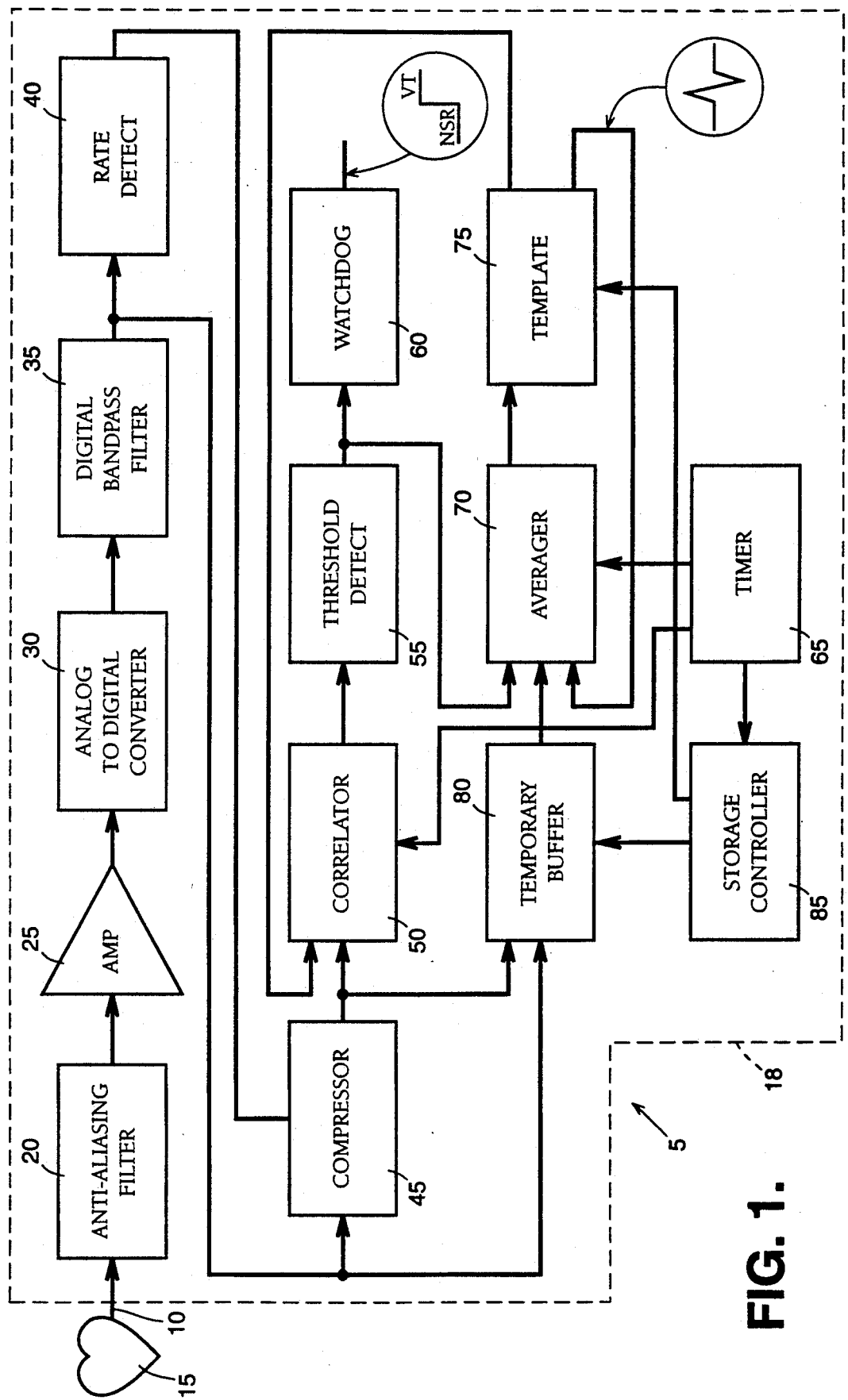
FIG. 1 is a block diagram of the preferred embodiment of the invention, in which a digital scanning correlator operates within a signal averaging system.

Only those parts of a cardiac control or diagnostic instrument which are necessary for an understanding of the present invention are shown in the drawings. Thus, although useable in a cardioverter/defibrillator, for example, the arrhythmia reversion mechanism of the latter is not shown.

FIG. 1 illustrates a preferred embodiment of a digital correlator or scanning correlator, shown generally at 5, in accordance with the present invention. This figure exemplifies the usage of the scanning correlator as the basic control element in a system for aligning cardiac signal waveforms for signal averaging by sampling electrocardiograms and comparing the sampled signals with stored signals composed of averaged normal sinus rhythm waveforms. Heart beat signals are sensed by electrodes (not shown) in the ventricle of the heart 15. The electrodes are electrically connected to leads 10 which extend to digital correlator electronics contained within a case 18. The scanning correlator 5 detects cardiac signals using one of the standard configurations in cardiac pacing: bipolar, unipolar tip-case or unipolar ring-case. Unipolar signals, arising from cardiac potentials accumulated over a larger surface of the ventricle, generally contain more information than bipolar signals, providing a more reliable correlation coefficient. On the other hand, bipolar signals offer better rejection of muscle and motion artifacts and noise, and provide the most detailed signal description of the electrophysiological state from a localized region of the ventricle.

The signal on the leads 10 is input to a low pass anti-aliasing filter 20 with a maximum high frequency cutoff of about 125 Hz. In the field of signal processing, the sampling theorem states that an analog signal, such as the signal applied to the anti-aliasing filter 20, is uniquely described by a set of uniformly spaced discrete (digital) samples taken at a particular sampling frequency, as long as no signal energy exists at frequencies greater than or equal to half this sampling frequency. The rate of half the sampling frequency is called the "folding frequency" because signals containing energy components at frequencies higher than the folding frequency, when sampled at the sampling frequency, will contribute a noise component to a reconstructed signal at the sampling frequency less the signal frequency. This noise is called aliasing noise. The high frequency cutoff (125 Hz) of the anti-aliasing filter is selected to correspond to a folding frequency appropriate for a sampling frequency of 250 Hz. Although the anti-aliasing filter cutoff is chosen to correspond to the folding frequency in the preferred embodiment of the invention, a cutoff frequency ranging down to 25 Hz or lower is prudent for practical filter designs.

The filtered signal passes through a unity gain amplifier 25 to an analog to digital converter 30 which digitizes the cardiac signal for sampling at 250 Hz. The correlator limits the frequency of the digitized cardiac signal using a digital bandpass filter 35 to attenuate signals below 0.25 and above 11 Hz to remove line frequency noise at 50 Hz or 60 Hz, while retaining essentially all of the diagnostic information contained in a cardiac signal. In the preferred embodiment of the invention, the high frequency cutoff is set to the apparently low frequency of about 11 Hz. One reason for limiting the sampled signal to this range is to eliminate or reduce artifacts arising from the aliasing of line frequency noise into the desired signal. Although the original signal is sampled at a frequency of 250 Hz, data compression reduces the effective frequency to 50 Hz. Therefore, the high frequency cutoff is set lower than the effective folding frequency of 25 Hz (half the effective sampling frequency). A cutoff frequency as low as 11 Hz prevents aliasing in filtering circuits having common attenuation characteristics to yield an appropriately small output at 25 Hz.

A signal correlator must perform many computations when calculating a single correlation coefficient. The service lifetime of an implantable device is inversely proportional to the amount of numerical processing it must perform. A rate detect block 40 controls whether the correlator is active at a given time. This embodiment of the invention may restrict the operation of signal averaging to take place only when the heart is functioning at a particular range of rates. For example, if an averaged signal is processed during cardiac cycles including some cycles which are characterized by ventricular tachycardia and other normal sinus rhythm cycles, the fine detail sought by performing signal averaging may be obscured. Rate detect block 40 determines the current heart rate and compares it to one or more predetermined rate limits. If the rate is within a pair of rate limit values, rate detect block 40 directs the averaging of the acquired signal by assigning the acquired signal to add to a particular averaging memory buffer. The device may include multiple averaging memories, although for simplification, the invention is described to include only a single averaging memory. If a device includes multiple averaging memories, the predetermined rate limits may also specify lower and upper rate limits, beyond which no signal averaging occurs to conserve energy in an implantable device.

Periodically (about once per day), the digital correlator should update the correlation template. While updating the correlation template, the rate detect block 40 controls the operations of the correlator in a different manner as compared to the operations during scanning correlation. During template updating, the rate detect block 40 prevents contamination of the template waveform with nonstandard cardiac rhythms by disabling the correlator when the cardiac rate is high. Only if the rate is characteristic of normal sinus rhythm does the rate detect block enable the correlator to update the normal sinus rhythm template.

The 250 Hz samples of digitized cardiac signal pass from the bandpass filter 35 to a temporal data compressor 45, and selectively to a temporary buffer 80 if the latter is enabled by a storage controller 85. Scanning correlation processing requires a number of computations, which number is approximately proportional to the square of the sample rate for both the input data and the correlation template, motivating a reduction in effective sampling rate as much as possible. The amount of possible reduction in effective sampling rate depends on the highest frequency content of the signal. For cardiac waveforms using the described compression method, compression to 50 Hz produces an accurate signal for analysis and storage. The temporal data compressor eliminates four of every five samples, saving from each group of five samples only the sample with the maximum excursion from the last saved sample, to decimate (reduce) the signal from a frequency of 250 Hz to 50 Hz.

The data compression procedure of block 45 analyzes a predetermined number of input samples to find the value of the sample having the maximum excursion, positive or negative, from the most recent output sample. The predetermined number of input samples for each output sample is the compression ratio. The output has a uniform sample period because a fixed number of input samples are evaluated for each of the output samples.

Figure 2:
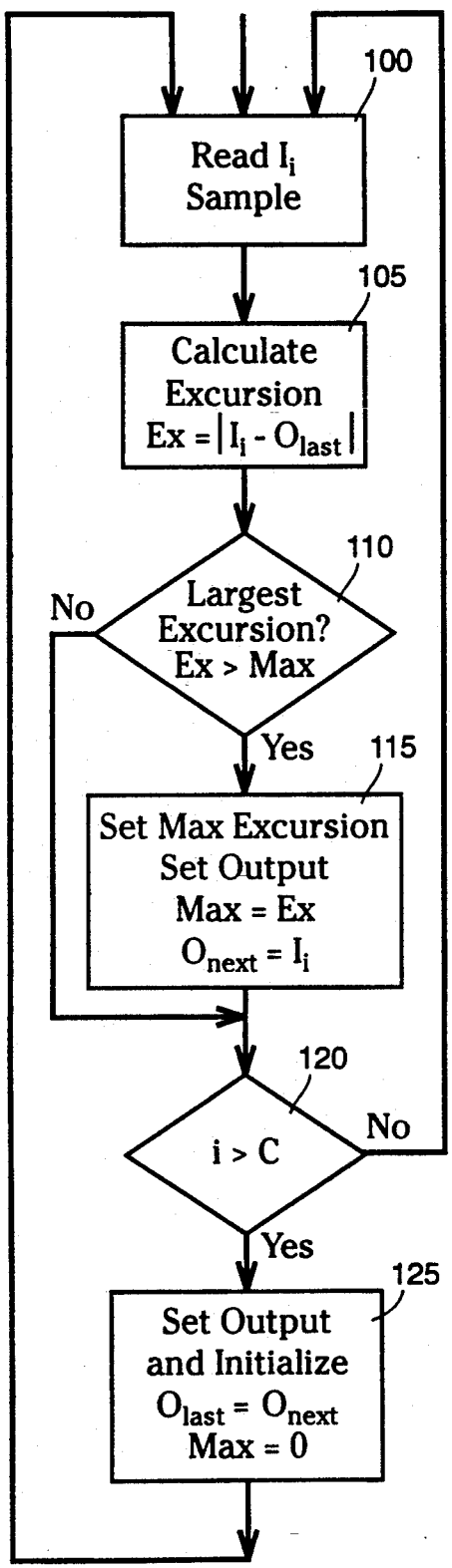
FIG. 2 is a flow chart illustrating the operational steps for one example of the data compression procedure.

FIG. 2 illustrates one embodiment of the data compression procedure. In block 100, the compressor reads the input data sample, $I_i$, beginning with the first sample ($i=1$). In block 105, the compressor calculates the excursion, Ex, from the output data sample from the last iteration of the procedure, $O_{last}$, according to the equation (1) below:

$$Ex = |I_i - O_{last}|. \tag{1}$$

If the excursion, Ex, is greater than the maximum excursion, Max, in block 110, then the compressor (in block 115) sets the value of Max to Ex and temporarily stores the input sample, $I_i$, in a memory location for the next output data sample, $O_{next}$. Following this, or if the excursion Ex is less than the maximum excursion Max in block 110, the procedure returns via block 120 to block 100 to perform blocks 100 to 115 in a loop C times, where C is the compression ratio. After looping C times, as controlled by logic block 120, the compressor returns the result, $O_{next}$, to the calling procedure and sets the value of $O_{last}$ to $O_{next}$ to prepare for compression of the next sample in block 125.

Figure 3:
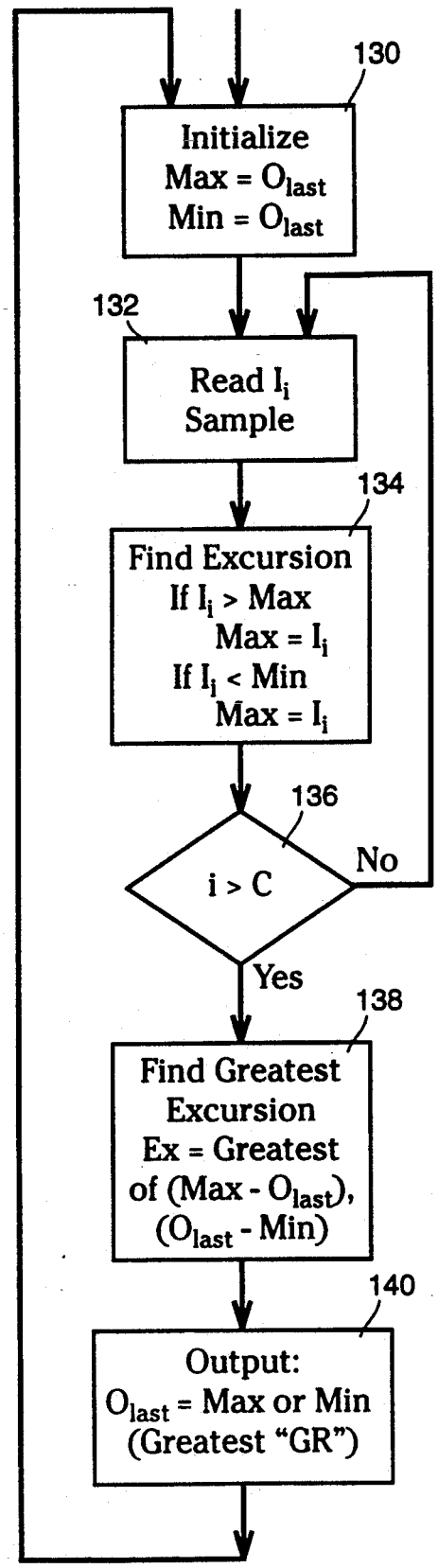
FIG. 3 is a flow chart illustrating the operational steps for a second example of the data compression procedure.

FIG. 3 illustrates a second embodiment of the data compression procedure which is more efficient in conserving the number of computing steps for some microprocessors or controllers because it avoids the absolute value determination and subtraction within its searching loop. In block 130, the compressor sets both the maximum sample, Max, and the minimum sample, Min), to the value of the output data sample from the last iteration of the procedure, $O_{last}$. The procedure enters the test loop beginning in block 132. The procedure performs blocks 132 to 136 within the loop C times as controlled by the logic test in block 136, where C is the compression ratio. Within the loop in block 132, the compressor accesses the input data sample, $I_i$, beginning with the first sample (i=1). In block 134, the procedure updates the maximum and minimum sample values by comparing $I_i$ to Max and Min. For a given sample I at time i, if Max is less than $I_i$, it is set to $I_i$. If Min is greater than $I_i$, it is set to $I_i$. After looping C times, in block 138 the compressor determines the positive and negative excursions, respectively, by subtracting $O_{last}$ from Max and by subtracting Min from $O_{last}$. The compressor stores the greater of the positive and negative excursions in $O_{last}$ to prepare for compression of the next sample and returns this value as the compressor result to the calling procedure in block 140.

Data compression to 50 samples per second (20 msec sample period) using this procedure preserves the majority of the information content of intracardiac electrogram data. Data compression to 25 samples per second or less results in visual degradation of the signal including the loss of temporal resolution less than the sampling period, temporal (phase) shift in the output data, and temporal widening of fast events such as a QRS complex.

The procedure for temporally compressing the template and cardiac signal sequences is simple and efficient, requiring few computations for each input sample, and provides for conservation of energy by reducing the total number of computational steps per cardiac cycle. Despite the reduction in data volume, this compression method maintains the accurate temporal, amplitude, and morphology information contained within the original cardiac signal.

In addition, this compression procedure permits "a priori" specification of the compression factor and, therefore, the computation requirements. The distinctive data compression scheme conserves information by preserving, respectively, uniform input and output sampling periods and the major amplitude changes in the original data during the rapid deflections of the QRS complex. The compression procedure is simple to implement, executes in real-time on most or all processors for signals with a bandwidth standard in cardiology applications, and provides for large compression ratios while preserving the fidelity of peak amplitude variations and waveform morphology in cardiac signals. By preserving peak amplitude variations within the compression period the procedure has no inherent low pass filter effect (at the expense of retaining large amplitude noise spikes). Data compressing in this nonlinear manner appears to avoid the Nyquist sampling limitations (at the expense of a slight temporal phase shift in the output data).

The uniform sampling period, which is inherent in the data compressor of the present invention, is advantageous because it requires no special decoding algorithm prior to restoring the signal for processing or display.

Signal processors outside the field of cardiac control and monitoring devices normally perform data compression to reduce data storage and transmission requirements rather than to limit the number of computations in determining a correlation function.

The key to reducing computations in scanned correlation is to temporally compress the template and input waveforms before performing the correlation computation. To perform a correlation computation requires TX multiplications per second where T is the number of samples in the template and X is the sample rate of the cardiac signal. The number of multiplications increases with the square of the sample rate. By compressing the template and sample cardiac signal each by a factor of 5, the necessary number of multiplications decreases by a factor of 25. The data compression technique of the present invention provides for compression ratios of 20:1, thereby dramatically reducing the number of necessary computations, while yielding results after correlation which are nearly identical to results produced by the correlation of signals which have not been compressed.

Data compression techniques are normally utilized to reduce data storage requirements of a device. In the present invention, the purpose of data compression is to reduce computational requirements and conserve the energy expenditure of an implantable device to more efficiently use the limited battery life.

Again referring to FIG. 1, where a 5 to 1 compression ratio is utilized, the compressor output of block 45 is a 50 Hz digital signal which passes to a correlator 50 and possibly to temporary buffer 80, if the latter is enabled by storage controller 85. Temporary buffer 80 and storage controller 85 provide for the storage of compressed or noncompressed waveforms for some scanning compressed correlator applications. The correlator 50 correlates the input signal with a template segment of previously sampled and averaged normal sinus rhythm waveform data (NSR).

The standard correlation formula is shown in equation (2), below:

$$R = \frac{\sum_{i=0}^{N} (T_i - \mu_T)(X_i - \mu_X)}{\sqrt{\sum_{i=0}^{N} (T_i - \mu_T)^2 \sum_{i=0}^{N} (X_i - \mu_X)^2}} \quad (2)$$

where R is the correlator result for each data sample, each $T_i$ is a template sample at time i, each $X_i$ is a cardiac signal sample, $\mu_T$ and $\mu_X$ are the means for the template samples T and the cardiac signal samples X, respectively, and N is the template length. Standard correlation requires a square root operation in the denominator of the equation, which although possible to accomplish, would be difficult to implement in the limited energy conditions of an implantable device. Rather than performing the square root operation, the preferred embodiment of the invention squares the numerator and denominator of the right side of the equation, eliminating the square root operation, and leaving the correlation result R in its squared form $R^2$. This squared form of R, termed the "correlation coefficient" is used as a surrogate for the standard result. By avoiding the computationally-intensive square root operation at the cost of only one additional multiplication operation (the squaring of the numerator of the right hand side of the equation), this method of analysis promotes efficiency and power conservation. Since the correlation coefficient $R^2$ is in the squared form, it always takes a positive value.

Standard correlation requires the determination of the means, $\mu_T$ and $\mu_X$, for both the template T, and cardiac signal X, samples. The preferred embodiment of the invention eliminates the correction for the mean since high pass filtering within the aforementioned bandpass filter substantially removes the DC component of the signal, forcing the mean to zero. By removing the mean correction, this technique saves N subtraction operations (where N is the template length) for each sample in the input waveform, X, and simplifies the computation for each sample. Note that this simplification is only possible when the length of the template is not too small in relationship to the cardiac cycle length. For this reason, the correlator within the preferred embodiment of the invention monitors the heart rate and does not allow template lengths shorter than about 10% of the minimum cardiac cycle length.

These two simplifications change the correlation function for calculating a new correlation coefficient, $R^2$, as shown in equation (3), below:

$$R^2 = \frac{\left(\sum_{i=0}^{N} T_i X_i\right)^2}{\sum_{i=0}^{N} T_i^2 \sum_{i=0}^{N} X_i^2}. \tag{3}$$

Figure 4:
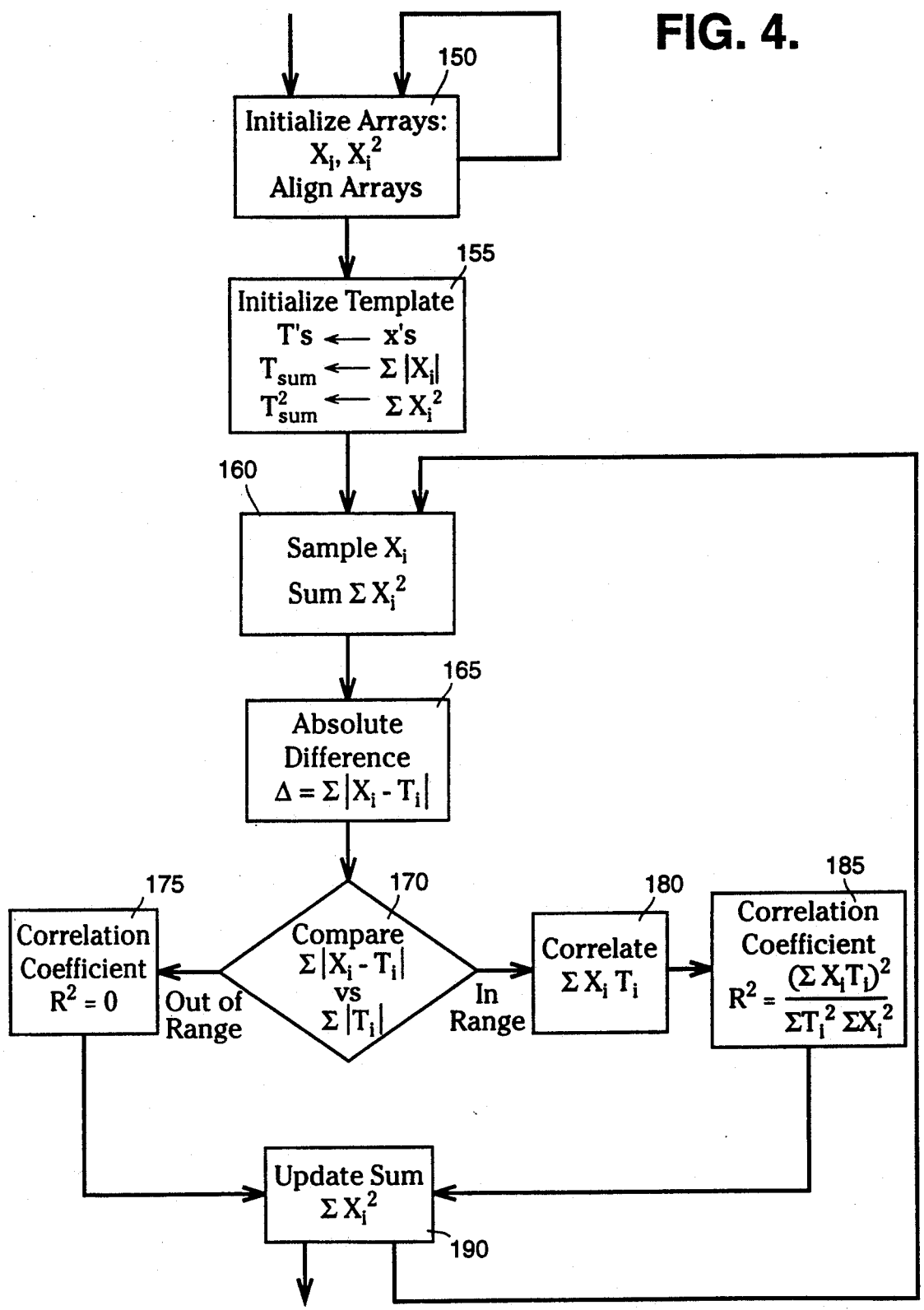
FIG. 4 is a flow chart illustrating the operational steps for the preferred embodiment of the scanning correlation procedure.

The flowchart in FIG. 4 describes the operations performed by the correlator. Before beginning the correlation function, the correlator first initializes the cardiac signal sample arrays, $X_i$ and $X_i^2$, and the scalar value of $\Sigma X_i^2$ over the most recent N samples. In the initialization operation, each element of each array is set to zero, as is the scalar $\Sigma X_i^2$. The size of the $X_i$ and $X_i^2$ sample arrays is based on the expected number of 250 Hz samples for a sampled interval within a cardiac cycle of normal duration. For example, a common size for $X_i$ and $X_i^2$ arrays for normal sinus rhythm cardiac signals may be defined to include 80% of a typical resting heart rate escape interval, a duration of approximately 700 milliseconds. Therefore, a sample rate of 250 Hz, which is temporally compressed to 50 Hz has a compressed sample duration corresponding to each 20 millisecond interval. There are 35 compressed samples for each 700 millisecond array duration. If each sample is stored in a single eight bit byte, each array $X_i$ and $X_i^2$ is stored in 35 bytes. The size of the template arrays, $T_i$ and $T_i^2$, matches that of the arrays $X_i$ and $X_i^2$.

Block 150 is a cardiac signal sampling loop which initializes the arrays necessary for correlation processing and aligns the signal waveform within the arrays to affirm that the R-wave of the cardiac signal is within the template. In the proposed example, the alignment process establishes a 700 millisecond duration template array ending 600 milliseconds after sensing an R-wave. Within the loop, the correlator samples cardiac signal data at 250 Hz, discards four of five samples according to the data compression procedure, stores the remaining data sample in the $X_i$ array, squares the sample and stores the result in the $X_i^2$ array. Block 155 performs the second initialization step of storing the template selected in sampling block 150 in the template array, $T_i$. Block 155 also determines the sum of the elements in the array $T_i^2$ and stores the result in the scalar parameter, $\Sigma T_i^2$ for N template samples. The correlator derives these data during template formation in initialization, and maintains template validity against physiological changes over time by periodic updates.

The correlator in one embodiment of the invention establishes the template length to be 80% of the average normal sinus rhythm cardiac cycle length. Alternatively, the correlator may utilize a variable template length, which is set according to the purpose and application of the scanning correlator.

The correlation coefficient, $R^2$, is normally independent of the cardiac signal amplitude because the $\Sigma X_i^2$ factors appear in both the numerator and the denominator of the correlation equation, as may be seen in equation (3) above. Therefore, it is possible that correlation of noise in the cardiac signal or, more importantly, correlation of random nonphysiological signals obscuring the true cardiac signal, with the template can create an inappropriately large correlation coefficient. These random nonphysiological signals are low level signals which may correlate highly with the template due to the statistical nature of the correlation operation, but are not considered to be true physiological signals.

The correlator includes an absolute difference measurement to detect and respond to these nonphysiological signals. For each sample, $X_i$, the correlator determines the absolute value of the difference between the cardiac signal sample and the template sample. The correlator then sums the difference magnitudes for the entire sample length, N, to determine the nonphysiological signal measurement for the current cardiac cycle.

To determine the relationship of the nonphysiological signal magnitude to the signal, the correlator compares the nonphysiological signal value to a normalization parameter, $T_{norm}$. The normalization parameter is chosen to be the sum of the absolute values of the template samples for the length of the template because this averaged value of normal samples best approximates the expected signal magnitudes in the absence of nonphysiological signals. While initializing the template in block 155, the correlator determines the absolute value for each sample, $T_i$, and sums each value to create the normalization parameter, $T_{norm}$, as shown in equation (4), below:

$$T_{norm} = \sum_{i=0}^{N} |T_i|. \tag{4}$$

After initialization, control passes to block 160 which begins the cardiac signal sampling for correlation determination. To conserve energy in an implantable device, the preferred embodiment of the invention only performs the correlation function when necessary. For example, the correlation process may pause until the intrinsic cardiac rate is within a predetermined test range. The correlator may maintain all parameters and arrays while the function is inactive.

In block 160, the correlator samples the data compressed cardiac signal and stores the result in $X_i$. The correlator also updates the $X_i^2$ array and sum by squaring the cardiac signal sample and adding it to the scalar $\Sigma X_i^2$, taken from (and stored back into) a memory location.

In block 165, the correlator determines the absolute difference between corresponding template and cardiac signal samples. The absolute difference determination, shown in statement (5) below, $$\sum_{i=0}^{N} |X_i - T_i|, \tag{5}$$

takes place within a loop which sums the difference magnitudes for each corresponding sample and template pair for all the samples in the cardiac cycle.

The correlator performs the noise test in block 170 by comparing the sum of the absolute differences determined in block 165 to the normalization parameter, $T_{norm}$. the sum of the absolute differences is too large (for example, 0.5 times the normalization parameter), the correlator determines that the system cannot determine the correlation coefficient due to the presence of excessive nonphysiological signals. In this case the correlator sets the correlation coefficient to zero in block 175. Otherwise, the correlator derives the correlation coefficient $R^2$ via blocks 180 and 185.

Assuming that the sum of the absolute differences in block 170 is within an acceptable range (i.e., the nonphysiological signal amplitude is not too large), the correlator next determines the correlation numerator product in an iterative manner for each sample in the template. Block 180 includes the correlation numerator loop calculation, wherein the correlator multiplies each element in the cardiac signal sample array, $X_i$, by the corresponding element in the previously stored template array, $T_i$, then sums these products for all N array elements.

In block 185, the correlator determines the correlation coefficient by squaring the numerator value from block 180, shown in statement (6) below, $$\left( \sum_{i=0}^{N} ((X_i)(T_i))^2 \right), \tag{6}$$

and divides it by the product from block 160, shown in statement (7) below, $$\sum_{i=0}^{N} (X_i)^2, \tag{7}$$

multiplied by the product from block 155, shown in statement (8) below, $$\sum_{i=0}^{N} (T_i)^2. \tag{8}$$

In block 190, the correlator prepares for processing the next sample in block 160 by reducing the value of the memory location, shown in statement (9) below, $$\sum_{i=0}^{N} (X_i)^2, \tag{9}$$

by the value of the oldest sample in the array $X_i^2$. In this manner, the correlator reduces the number of computations by maintaining the sum during sampling, then subtracting the oldest sample from the sum and adding the newest sample for each sampling cycle.

This correlation method requires N+34 multiplications, 1 division and N+5 additions per sample, i, where N is the number of samples in the template. The device may reduce computations in multiplication either by performing the correlation function in hardware, by referencing lookup tables in memory indexed by the multipliers and multiplicands or by setting the product to a minimum value if either or both the multiplier and multiplicand are too small (or negative).

Two facts allow the device to further reduce the computations for scanning correlation. First, the heart exhibits a refractory period where it is unexcitable to electrical stimuli. Secondly, the electrogram is generally a periodic waveform. A device performing operations not requiring the maximum correlator value for further processing may reduce computations by defining a refractory period following each detected heartbeat, wherein the device does not measure the correlation function. A detected heartbeat, as defined when the correlator output is greater than a predetermined threshold value, signals a time when the correlator can immediately cease operations. The duration of this inactive period may be set by external programming (in a device equipped with communication capabilities as known in the art of heart pacemakers).

The device may automatically and dynamically set the inactive period duration to a value inversely proportional to the measured heart rate or proportional to the template length. Alternatively, the device may trigger the inactive period using an external heartbeat identifier such as a hardware implemented high pass filter and threshold comparator similar to the sense inhibit which is standard in the art of cardiac pacemakers. Processing in this manner requires data storage to permit analysis of samples occurring prior to the trigger signal.

After correlating the cardiac signal with the normal sinus rhythm template in block 50 (FIG. 1), the digital correlator compares the correlation coefficient with a predetermined threshold value in block 55. The threshold is a programmed or automatically adapting threshold value.

If the correlation coefficient is smaller than the threshold value, indicating a lack of similarity between the correlation coefficient and the normal sinus rhythm template, the device does not perform signal averaging but, instead, control passes to the watchdog 60. The watchdog 60 may be programmed to detect harmful cardiac arrhythmias. For example, in addition to performing signal averaging, programming of the device may specify a particular set of cardiac rates and template morphologies which may be characteristic of ventricular tachycardia or fibrillation. A predetermined criterion is defined which includes an analysis of cardiac rates, correlation coefficients characterizing one or more template morphologies, and the duration these rates and correlation coefficients are sustained. The watchdog 60 tests the patient's cardiac function according to these criteria and, in response, may initiate a notification signal to the patient.

If the correlation coefficient is greater than the threshold value, showing similarity of the correlation coefficient with the normal sinus rhythm template, and a timer 65 determines it is time for a periodic signal averaging update, control passes to the averager block 70.

Patient morphologies may change over time due to progression of disease. These gradual changes in morphology necessitate periodic updating of the templates to adapt each template to the new morphology and permit reliable operation of the correlator. For example, the correlator must maintain a template of normal sinus rhythm (NSR) by performing periodic template updating when the heart is functioning at normal heart rates to insure that the NSR template does not adapt to ventricular tachycardia. The timer 65 may activate the correlation procedure on the order of once per day (a reasonable interval, considering the balance between normal signal variability and power consumption requirements). The heart must be beating with an appropriate rate for the device to allow template updating. For example, the timer 65 will activate the correlation procedure only in the presence of normal sinus rate activity to maintain the normal sinus rhythm template. When the rate detector 40 indicates that the heart is functioning at a normal sinus rhythm, the device periodically (timed by timer 65) updates an averaged normal sinus rhythm waveform, by detecting R-waves of consecutive cardiac cycles and determining the cardiac rate from the interval between the R-waves in rate detect block 40. After determining the current heart rate, the device then correlates the segments of cardiac signals in block 50, and accumulates and averages selected segments for a predefined number of cardiac cycles in block 70. The digital correlator updates the averages only if the correlation coefficient exceeds the appropriate threshold (for example, 0.95) for the normal sinus heart rhythm as determined by rate detect block 40.

When the averager 70 has accumulated data for the desired number of cycles, control passes to block 75 where the digital correlator stores the template by storing the averaged current $X_i$ array into the $T_i$ array and storing the scalar $\Sigma X_i^2$ value into the scalar $\Sigma T_i^2$ memory location. The number of samples in the template segment depends on the natural sinus rate and the duration of its associated cardiac interval. The template length is preset to a percentage (from 10% to 80%) of the average cardiac interval. The correlator performs cardiac signal sampling to determine the template in a manner such that each template includes the R-wave and as much of the T-wave following the R-wave as possible, since the device predicts when the next R-wave will occur from an average of cardiac intervals of recently occurring cycles and begins sampling prior to the predicted R-wave time. If an R-wave does not occur within the sampling time or if the correlation coefficient of a given sample does not meet a threshold criterion (for example 0.9), the device does not update the accumulated average.

FIGS. 5A through 5F illustrate comparisons of the results obtained by correlating cardiac signals when a cardiac electrogram and a template are not data compressed (FIGS. 5A through 5C), and when the electrogram and template are data compressed (FIGS. 5D through 5F). These comparisons are accomplished by sampling actual cardiac signal samples and performing a computer simulation of the correlation procedure. When the electrogram and template are data compressed, there is a considerable savings in the computational burden. This is afforded by the procedure of compressing the data prior to correlation using the data compression scheme of the present invention. This savings in computational burden is accomplished at the cost of only a slight degradation in the correlation coefficient.

The scanning correlation coefficient of FIG. 5C is produced by correlating a normal sinus rhythm signal (FIG. 5A) with a normal sinus rhythm template (FIG. 5B), both of which are sampled at a data rate of 1000 samples per second. The correlation procedure may be visualized by sliding the template waveform of FIG. 5B along the cardiac signal waveform of FIG. 5A. The correlation coefficient of FIG. 5C is at its maximum value at each position of the template in which the morphologies of the template waveform and the cardiac signal most closely match.

Data compression of the same cardiac signal and the identical template at a 20:1 ratio reduces the effective sampling rate to 50 samples per second. Subsequent correlation of the compressed normal sinus rhythm signal (FIG. 5D) with the compressed sinus rhythm template (FIG. 5E), yields the scanning correlation coefficient of FIG. 5F. Analysis of the compressed cardiac signal waveform of FIG. 5D indicates that the compressed data retains most of the signal morphology information contained within the original data, although there is some loss of low amplitude signal information and a small degree of temporal distortion, particularly in the vicinity of the QRS complex when fast signal changes occur. The readily apparent similarity between the noncompressed and compressed correlation coefficient waveforms (FIGS. 5C and 5F, respectively) illustrates the usefulness of compressed scanning correlation, considering the large savings in data storage requirements (a twenty times reduction) and computational burden (a 400 times reduction).

The flow diagram of FIG. 6 illustrates the procedure for performing cardiac waveform alignment for signal averaging using the scanning correlation technique. The blocks within the digital correlator 5 of FIG. 1 may be configured to perform the signal averaging operations of FIG. 6. The digital correlator 5 performs different functions by means of variations in control of the storage controller 85, timer 65 and rate detector 40 in FIG. 1. For signal averaging, the digital correlator 5 is utilized solely to provide accurate alignment of features (most commonly, the R-wave) within a single cardiac cycle. When the periodic cardiac waveforms are aligned, the signal averager accumulates and averages the waveforms from multiple cardiac cycles to reduce the influence of beat to beat changes and other changes not synchronized to the electrocardiogram. Signal averaging allows detection of low amplitude periodic signals which otherwise are hidden in noise.

Referring to FIG. 6, the signal averaging alignment procedure begins by acquiring noncompressed cardiac signal samples (intracardiac electrogram or IEGM) in block 300. Block 305 stores the noncompressed electrogram. Block 310 temporally compresses the IEGM data using the previously described nonlinear compression method (block 45 of FIG. 1) and block 315 correlates the compressed IEGM data with a compressed NSR template. The threshold step of block 320 provides an efficient means for determining the initial coarse or estimated fiducial time, which occurs at the sample time when the correlation result reaches the threshold value. Block 325 stores this fiducial time result. Block 330 performs piecewise correlation of a noncompressed template of NSR with a small segment of the noncompressed waveform (which was stored in block 305). This small segment includes samples which are closely adjacent to and before and after samples which correspond to those which occur at the sample time when the correlation result reaches the threshold value. The noncompressed signal and template are aligned according to the estimated fiducial time from block 325. Block 335 detects the peak correlation coefficient and sets the time of this peak as the accurate or fine fiducial time result. The alignment procedure makes this result available to the procedure which performs signal averaging.

The compression routine described herein results in a loss of temporal information which is finer in detail than the sample period of the compressed data. Therefore, the scanning correlation routine alone is not suitable for determining the fiducial time which defines the precise alignment between the sampled and averaged waveforms, which is required for signal averaging. It does, however, provide a very efficient procedure for determining the approximate fiducial time. A procedure using a two-pass technique for fiducial time determination will provide the required accuracy. The first pass computes the scanning correlation on compressed data. The fiducial time from the first pass is set as the time of the peak correlation coefficient following a threshold determination of the correlation value. The second pass refines this fiducial time by computing the scanning correlation on the noncompressed data for only a short period (typically plus and minus two compressed sample periods) around the first pass fiducial time. The refined fiducial time is the time of the peak of this waveform. A signal averaging routine will use the refined fiducial time to align signals for averaging. This two-pass correlation technique is important for medical devices which perform signal averaging of sensed cardiac waveforms for various diagnostic and therapeutic purposes. For example, it is desirable to detect cardiac arrhythmias by analyzing cardiac late potentials which have a signal magnitude much smaller than that of background noise. Late potentials appear only faintly, if they appear at all, in sensed electrocardiograms. Because late potentials occur only at a known portion of the electrocardiogram, signal averaging of this portion of the waveform for multiple cardiac cycles will diminish background noise sufficiently to enable late potential analysis.

This technique for signal averaging may increase the computational efficiency of aligning the cardiac waveforms on the order of 100 times. For example, to find fiducial time to an accuracy within 1 msec, the device computes the scanning correlation using 1 kHz data. Compression reduces the data by a factor of 20 for both the template and the sample electrogram, resulting in a 400 times decrease in computations on the first pass. The second pass refines the fiducial time using the original data. The overall decrease in CPU time is over 100 times.

From the foregoing discussion, it is apparent that the present invention provides a signal correlation system within a cardiac control and monitoring device which accomplishes substantial improvement in conserving data storage requirements, computational burden, and energy while providing an effective means for providing alignment of periodic cardiac signals for signal averaging.

Although the invention is described with reference to a particular embodiment, it is to be understood that this embodiment is merely illustrative of the application of the principles of the invention. Numerous modifications may be made therein and other arrangements may be devised without departing from the true spirit and the scope of the invention.

We claim:

1. A method of aligning cardiac electrical signal waveforms from a patient's heart to facilitate signal averaging, comprising the steps of:
   sensing and sampling cardiac electrical signals and, in response thereto, determining a heart rate for identifying the patient's cardiac state;
   when the patient's heart is functioning in a known cardiac state, storing a time sequence of template samples, temporally compressing said time sequence of template samples, and storing a time sequence of said temporally compressed template samples;
   monitoring subsequent cardiac electrical signals by storing a time sequence of cardiac signal samples, temporally compressing said time sequence of cardiac signal samples, and storing a time sequence of temporally compressed cardiac signal samples;
   determining a coarse alignment timing marker for a cardiac cycle of said subsequent cardiac electrical signals by mutually scan correlating said temporally compressed cardiac signal samples with said temporally compressed template samples, and by comparing resulting correlation coefficients to locate a maximum correlation coefficient indicative of signal alignment of said compressed template with said compressed cardiac signal; and
   determining a fine alignment timing marker for said cardiac cycle of subsequent cardiac electrical signals by mutually scan correlating those of said noncompressed cardiac signal samples which are closely adjacent to samples which correspond to the maximum correlation coefficient with those of said noncompressed template samples which are closely adjacent to samples which correspond to the maximum correlation coefficient, and by comparing resulting correlation coefficients to locate a maximum correlation coefficient indicative of signal alignment of said noncompressed template with said noncompressed cardiac signal.

2. A method according to claim 1, further comprising the step of highpass filtering said sensed and sampled cardiac electrical signals to substantially eliminate the mean amplitude of each of said template and cardiac signal sample sequences.

3. A method according to claim 2, wherein, when deriving said correlation coefficients, said scan correlating sub-step of said coarse alignment timing marker determining step disregards the mean amplitude of each of the temporally compressed template samples and the temporally compressed cardiac signal samples, and said scan correlating sub-step of said fine alignment timing marker determining step disregards the mean amplitude of each of the noncompressed template samples and the noncompressed cardiac signal samples.

4. A method according to claim 1, wherein each of said temporally compressing steps comprises the substeps of:

determining the differences between the most recent sample of said temporally compressed time sequence and each of a predetermined number of consecutive noncompressed samples of said sensed cardiac electrical signal sequence, wherein said predetermined number is a compression ratio;

mutually comparing said differences to identify the sample in said sensed cardiac electrical signal sequence associated with the largest difference; and setting the current compressed sample to the value of said identified sample.

5. A method according to claim 3, wherein each of said temporally compressing steps comprises the sub-steps of:

subtracting each of a predetermined number of consecutive noncompressed samples of said sensed cardiac electrical signal from the most recently determined compressed sample, wherein said predetermined number is a compression ratio;

storing each of said noncompressed samples and its associated absolute difference value from each subtracting step result;

mutually comparing each of said stored absolute difference values to determine the largest absolute difference; and setting the current compressed sample to the value of the stored noncompressed sample associated with the largest absolute difference.

6. A method according to claim 1, wherein said step of storing a time sequence of template samples comprises the sub-steps of:

sampling a first sequence of cardiac electrical signals sensed when the heart is functioning in a known cardiac state;

storing said first sequence samples in a template memory;

sampling and storing subsequent cardiac electrical signals;

scan correlating said subsequent cardiac electrical signal samples with said template samples to derive a template correlation coefficient;

comparing said template correlation coefficient with a template threshold value;

if said template correlation coefficient is greater than said threshold value, aligning said subsequent cardiac electrical signal samples in time;

averaging said aligned subsequent cardiac electrical signal samples into said template; and repeating said sampling and storing, scan correlating, comparing, aligning, and averaging steps for a predetermined number of iterations.

7. A method according to claim 6, further comprising the steps of:

monitoring said cardiac electrical signals to determine an intrinsic heart rate and its associated intrinsic cycle length; and setting a template length limit restricting the size of the template to a predetermined percentage of said intrinsic cycle length.

8. A method according to claim 6, further comprising the steps of:

locating an R wave in said sequence of cardiac electrical signals; and aligning said first sequence samples in the template memory so that the R wave sample is stored in a predetermined sample location.

9. A method according to claim 7, further comprising the steps of:

locating an R wave in said sequence of cardiac electrical signals; and aligning said first sequence samples in the template memory so that the R wave sample is stored in a predetermined sample location.

10. A method according to claim 5, wherein said step of storing a time sequence of template samples comprises the sub-steps of:

sampling a first sequence of cardiac electrical signals sensed when the heart is functioning in a known cardiac state;

storing said first sequence samples in a template memory;

sampling and storing subsequent cardiac electrical signals;

scan correlating said subsequent cardiac electrical signal samples with said template samples to derive a template correlation coefficient;

comparing said template correlation coefficient with a template threshold value;

if said template correlation coefficient is greater than said threshold value, aligning said subsequent cardiac electrical signal samples in time;

averaging said aligned subsequent cardiac electrical signal samples into said template; and repeating said sampling and storing, scan correlating, comparing, aligning, and averaging steps for a predetermined number of iterations.

11. A method according to claim 10, further comprising the steps of:

monitoring said cardiac electrical signals to determine an intrinsic heart rate and its associated intrinsic cycle length; and setting a template length limit restricting the size of the template to a predetermined percentage of said intrinsic cycle length.

12. A method according to claim 10, further comprising the steps of:

locating an R wave in said sequence of cardiac electrical signals; and aligning said first sequence samples in the template memory so that the R wave sample is stored in a predetermined sample location.

13. A method according to claim 11, further comprising the steps of:

locating an R wave in said sequence of cardiac electrical signals; and aligning said first sequence samples in the template memory so that the R wave sample is stored in a predetermined sample location.

14. Apparatus for aligning cardiac electrical signal waveforms from a patient's heart to facilitate signal averaging, comprising:

means for sensing and sampling cardiac electrical signals and, in response thereto, determining a heart rate for identifying the patient's cardiac state;

means, activated when said heart rate determining means determines that the patient's heart is functioning in a known cardiac state, for storing a time sequence of template samples, temporally compressing said time sequence of template samples, and storing a time sequence of said temporally compressed template samples;

means for monitoring subsequent cardiac electrical signals by storing a time sequence of cardiac signal samples, temporally compressing said time sequence of cardiac signal samples, and storing a time sequence of temporally compressed cardiac signal samples;

means for determining a coarse alignment timing marker for a cardiac cycle of said subsequent cardiac electrical signals, said means including means for mutually scan correlating said temporally compressed cardiac signal samples with said temporally compressed template samples, and means for comparing resulting correlation coefficients to locate a maximum correlation coefficient indicative of signal alignment of said compressed template with said compressed cardiac signal; and means for determining a fine alignment timing marker for said cardiac cycle of subsequent cardiac electrical signals, said means including means for mutually scan correlating those of said noncompressed cardiac signal samples which are closely adjacent to cardiac signal samples which correspond to said maximum correlation coefficient with those of said noncompressed template samples which are closely adjacent to template samples which correspond to said maximum correlation coefficient, and means for comparing resulting correlation coefficients to locate a maximum correlation coefficient indicative of signal alignment of said noncompressed template with said noncompressed cardiac signal.

15. An apparatus according to claim 14, further comprising:

means for highpass filtering said sensed and sampled cardiac electrical signals to substantially eliminate the mean amplitude of each of said temporally compressed template and cardiac signal sample sequences.

16. An apparatus according to claim 15, wherein said scan correlating means of said means for determining a coarse alignment timing marker disregards the mean amplitude of each of the temporally compressed template samples and the temporally compressed cardiac signal samples, and wherein said scan correlating means of said means for determining a fine alignment timing marker disregards the mean amplitude of each of the noncompressed template samples and the non-compressed cardiac signal samples.

17. An apparatus according to claim 14, wherein each of said temporally compressing means further comprises:

means for subtracting each of a predetermined number of consecutive noncompressed samples of said sensed cardiac electrical signal from the most recently determined compressed sample, wherein said predetermined number is a compression ratio;

means for storing each of said noncompressed samples and its associated absolute difference value from each subtraction result;

means for mutually comparing each of said stored absolute difference values to determine the largest absolute difference; and means for setting the current compressed sample to the value of the stored noncompressed sample associated with the largest absolute difference.

18. An apparatus according to claim 16, wherein each of said temporally compressing means further comprises:

means for subtracting each of a predetermined number of consecutive noncompressed samples of said sensed cardiac electrical signal from the most recently determined compressed sample, wherein said predetermined number is a compression ratio;

means for storing each of said noncompressed samples and its associated absolute difference value from each subtraction result;

means for mutually comparing each of said stored absolute difference values to determine the largest absolute difference; and means for setting the current compressed sample to the value of the stored noncompressed sample associated with the largest absolute difference.

19. An apparatus according to claim 14, wherein said means for storing a time sequence of template samples, further comprises:

means for sampling a first sequence of cardiac electrical signals sensed when the heart is functioning in a known cardiac state;

means for storing said first sequence samples in a template memory;

means for sampling and storing subsequent cardiac electrical signals;

means for scan correlating said subsequent cardiac electrical signal samples with said template samples to derive a template correlation coefficient;

means for comparing said template correlation coefficient with a template threshold value;

means, operative when said template correlation coefficient is greater than said threshold value, for aligning said subsequent cardiac electrical signal samples in time;

means for averaging said aligned subsequent cardiac electrical signal samples into said template; and means for repeating said sampling and storing, scan correlating, comparing, aligning, and averaging means for a predetermined number of iterations.

20. An apparatus according to claim 19, further comprising:

means for monitoring said cardiac electrical signals to determine an intrinsic heart rate and its associated intrinsic cycle length; and means for setting a template length limit restricting the size of the template to a predetermined percentage of said intrinsic cycle length.

21. An apparatus according to claim 19, further comprising:

means for locating an R wave in said sequence of cardiac electrical signals; and means for aligning said first sequence samples in the template memory so that the R wave sample is stored in a predetermined sample location.

22. An apparatus according to claim 20, further comprising:

means for locating an R wave in said sequence of cardiac electrical signals; and means for aligning said first sequence samples in the template memory so that the R wave sample is stored in a predetermined sample location.

23. An apparatus according to claim 18, wherein said means for storing a time sequence of template samples, further comprises:

means for sampling a first sequence of cardiac electrical signals sensed when the heart is functioning in a known cardiac state;

means for storing said first sequence samples in a template memory;

means for sampling and storing subsequent cardiac electrical signals;

means for scan correlating said subsequent cardiac electrical signal samples with said template samples to derive a template correlation coefficient;

means for comparing said template correlation coefficient with a template threshold value;

means, operative when said template correlation coefficient is greater than said threshold value, for aligning said subsequent cardiac electrical signal samples in time so that said template correlation coefficient takes a locally maximum value by scan correlating additional subsequent cardiac electrical signal samples;

means for averaging said aligned subsequent cardiac electrical signal samples into said template; and means for repeating said sampling and storing, scan correlating, comparing, aligning, and averaging means for a predetermined number of iterations.

24. An apparatus according to claim 23, further comprising:

means for monitoring said cardiac electrical signals to determine an intrinsic heart rate and its associated intrinsic cycle length; and means for setting a template length limit restricting the size of the template to a predetermined percentage of said intrinsic cycle length.

25. An apparatus according to claim 23, further comprising:

means for locating an R wave in said sequence of cardiac electrical signals; and means for aligning said first sequence samples in the template memory so that the R wave sample is stored in a predetermined sample location.

26. An apparatus according to claim 24, further comprising:

means for locating an R wave in said sequence of cardiac electrical signals; and means for aligning said first sequence samples in the template memory so that the R wave sample is stored in a predetermined sample location.

* * * * *